US007752540B2

(12) United States Patent
Lee et al.

(10) Patent No.: US 7,752,540 B2
(45) Date of Patent: Jul. 6, 2010

(54) INFORMATION SYSTEM FOR METABOLIC FLUX ANALYSIS USING EXTENSIBLE MARKUP LANGUAGE AND OPERATING METHOD THEREOF

(75) Inventors: Sang Yup Lee, Daejeon (KR); Hong Seok Yun, Seoul (KR); Dong Yup Lee, Yongin-si (KR); Seung Hyun Lee, Seoul (KR); Joon Woo Jeong, Gwangju (KR); Tae Yong Kim, Yongin-si (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 1088 days.

(21) Appl. No.: 11/148,907

(22) Filed: Jun. 9, 2005

(65) Prior Publication Data

US 2006/0224371 A1 Oct. 5, 2006

(30) Foreign Application Priority Data

Mar. 31, 2005 (KR) .................. 10-2005-0027215

(51) Int. Cl.
G06F 17/00 (2006.01)
(52) U.S. Cl. .................. 715/234; 715/255; 715/235
(58) Field of Classification Search .......... 715/234, 715/239, 235, 255
See application file for complete search history.

(56) References Cited

U.S. PATENT DOCUMENTS

| 7,146,564 | B2 * | 12/2006 | Kim et al. ............ 715/235 |
| 2002/0184264 | A1 * | 12/2002 | Berg et al. ............ 707/513 |
| 2003/0009099 | A1 * | 1/2003 | Lett et al. ............ 600/416 |
| 2003/0069908 | A1 * | 4/2003 | Anthony et al. ............ 707/513 |
| 2003/0121001 | A1 * | 6/2003 | Jeannette et al. ............ 715/513 |
| 2004/0205562 | A1 * | 10/2004 | Rozek et al. ............ 715/513 |
| 2005/0114398 | A1 * | 5/2005 | Naik et al. ............ 707/104.1 |
| 2005/0187717 | A1 * | 8/2005 | Paxson et al. ............ 702/19 |
| 2006/0147899 | A1 * | 7/2006 | Famili et al. ............ 435/4 |

OTHER PUBLICATIONS

Edwards et al., *The Journal of Biological Chemistry*, 274, 17410-6, 1999.
Nielsen, et al., *Bioreaction Engineering Principles*, Plenum Press, 1994.
Segre et al., *A Journal of Intergrative Biology*, vol. 7, 301-16, 2003.
Yun, Hongseok, et al., "MFAML:an XML-based Standard Format for Metabolic Flux Analysis," The 15th International Conference on Genome Informatics, Dec. 13-15, 2004.

* cited by examiner

*Primary Examiner*—Thu Huynh
(74) *Attorney, Agent, or Firm*—Steven J. Hultquist; Intellectual Property/Technology Law; Kelly K. Reynolds

(57) ABSTRACT

The present invention relates to an MFA (Metabolic Flux Analysis) information system using an XML (eXtensible Markup Language) and an operating method thereof. More specifically, the invention relates to an MFA information system and an operating method thereof, which generates, edits, stores and visualizes an MFA model feature and an MFA object using XML, and edits, stores and visualizes the result obtained by performing MFA based on the object. The present invention provides the MFA information system and method capable of generating, editing, storing and visualizing MFA model features and MFA objects using XML. Accordingly, MFA can be easily performed by utilizing advantages of XML, such as transplantation, reusability, deciphering, scalability, flexibility and effective data exchange, and thus the present invention can be applied to cell improvement using metabolic engineering.

10 Claims, 5 Drawing Sheets

INFORMATION SYSTEM FOR METABOLIC FLUX ANALYSIS USING EXTENSIBLE MARKUP LANGUAGE AND OPERATING METHOD THEREOF

CROSS-REFERENCE TO RELATED APPLICATIONS

This application claims priority under 35 USC 119 of Korean Patent Application No. 10-2005-0027215 filed Mar. 31, 2005.

BACKGROUND OF THE INVENTION

1. Field of the Invention

The present invention relates to an MFA (Metabolic Flux Analysis) information system using XML (eXtensible Markup Language) and an operating method thereof. More specifically, the invention relates to an MFA information system and an operating method thereof, which generates, edits stores and visualizes an MFA model feature and an MFA object using XML, and edits, stores and visualizes the result obtained by performing MFA based on the object.

2. Background of the Related Art

MFA is one of mathematical modeling techniques and simulations which are widely used. The mathematical models can be largely divided into a model including dynamic and regulating mechanism information and a model considering only the stoichiometry of biochemical reactions. The dynamic model predicts internal variations in a cell with the passage of time to accurately describe the dynamic state of the cell. However, it has a shortcoming of requiring lots of dynamic parameters.

MFA obtains an ideal metabolic flux space that cells can reach using only a set of metabolic mass balancing reactions and cell composition information. It is known that MFA can show the ideal metabolic fluxes without requiring dynamic information and satisfactorily describe or estimate behaviors of the cell (Edwards et al., *The Journal of Biological Chemistry*, 274, 17410-6, 1999; Nielsen, et al., *Bioreaction Engineering Principles*, Plenum Press, 1994).

MFA is a mathematical approach to detect variations in metabolic fluxes with the stoichiometry of metabolic reactions and the measurements of produced and consumed quantities of various metabolites. MFA is based on the quasi-stationary state assumption. It means that a variation in the concentration of metabolites in a cell could be ignored and the concentration could be constant because the variation in the concentration of the metabolites in a cell caused by external environment modifications is very immediate.

If all metabolites and metabolic pathways and stoichiometric matrix in each pathway ($S_{ij}^T$, metabolite i in the $j^{th}$ pathway) are known, a metabolic flux vector ($v_j$, flux of the $j^{th}$ pathway) can be calculated. A variation in a metabolite X with the passage of time can be represented by the sum of all metabolic reaction fluxes. When it is assumed that the variation in the metabolite X with the passage of time is constant, that is, on the assumption that metabolic reaction is under the condition of the quasi-stationary state, the variation in the metabolite X is defined as follows.

$$S^T v = dX/dt = 0$$

However, this equation is expanded to the following equation because only pathways are known and stoichiometric value (for each metabolite and pathway) and metabolic flux ($v_j$) are partially known in most cases.

$$S^T v = S_m v_m + S_u v_u = 0$$

This equation is divided into two matrixes; One is the matrix defined as the inner product of an experimentally known stoichiometric value ($S_m$(I×M), I is a total metabolic number and M is a total stoichiometrically-known reaction number) and a flux ($v_m$(M×I)). The other is the product of an unknown stoichiometric value ($S_u$(I×M)) by a flux ($v_u$(M×I)).

Here, when rank (Su) of the unknown flux vector (Su) is identical to or larger than U (that is, when the number of variables is identical to or smaller than that of the equation), the flux is obtained through matrix calculation. However, when rank (Su) of the unknown flux vector (Su) is larger than U (when a duplicate equation exists), an operation of checking consistency of all equations, accuracy of flux measurement values and propriety of quasi-stationary state is performed in order to calculate more precise values.

If the number of variables is larger than that of the equation, a unique optimum metabolic flux distribution is obtained using linear optimization that uses various physical and chemical constraints, such as restricting a specific metabolic flux value within a specific range etc., and a specific objective function, which is defined as follows.

minimize/maximize: $Z = \Sigma C_i V_i$

S.t. $S^T v = 0$ and $a_{min,i} \leq V_i \leq a_{max,i}$

Here, Ci represents a weight and Vi denotes a metabolic flux vector. Cell growth maximization, metabolite production maximization and by-product production minimization are generally used as the objective function.

MFA can be used for calculating the maximum production yield of a desired metabolite through which characteristic of a metabolic pathway inside a cell can be detected. When the characteristic of the metabolic pathway is grasped, a metabolic pathway required to be operated is detected and metabolic flux is operated using the most effective method by a strategy for operating the metabolic pathway, thus making it possible to produce a desired metabolite.

To handle these MFA elements, metabolic network information including metabolites, metabolic pathways and stoichiometric matrix in each pathway and metabolic condition information including metabolic flux measurement values, genetic and environmental conditions and physical and chemical constraint conditions are required.

There have been systems for generating, editing, storing and visualizing the aforementioned information. However, a system for generating, editing, storing and visualizing the information using XML that is a standard of data and documents on the Internet has not been reported yet. Although there was an attempt to insert annotating simple condition information into an XML structure, it only dealt with the information on the flux limits associated with each flux and there was no detailed reference for an XML schema structure and thus it was not easy to actually utilize (Segre et al., *A Journal of Intergrative Biology*, vol 7, 301-16, 2003).

SUMMARY OF THE INVENTION

Accordingly, the present invention has been made to solve the problems in the prior art, and it is an object of the present invention to provide a system and method for generating, editing, storing and visualizing an MFA model feature and an MFA object using XML and generating, editing, storing and visualizing the result obtained by performing MFA based on the object.

To accomplish the above object, in one aspect, the present invention provides an MFA information system capable of generating, editing, storing and visualizing an MFA model feature and an MFA object and editing, storing and visualizing the result obtained by performing MFA based on the MFA object. The MFA information system includes: an MFA model feature authoring tool for generating a new MFA model feature or generating DTD (Document Type Definition) or schema file of XML after collecting and editing the corresponding existing MFA model feature; an MFA object authoring tool for generating a new MFA object with reference to the DTD or schema file generated by the MFA model feature authoring tool or storing an edited MFA object in an XML file after editing the corresponding existing MFA object; and an MFA object analysis browser for reading the DTD or schema file of XML generated by the MFA model feature authoring tool and the XML file stored by the MFA object authoring tool to visualize the MFA object, carrying out MFA based on the MFA object, and visualizing by integrating the MFA result with MFA object information.

In the MFA information system according to the present invention, the MFA model feature authoring tool includes: a means of defining a new MFA model feature name, types of metabolic network information, metabolic condition information, MFA result information and MFA visualization information, a data type and a storing method; and a means of changing the related existing MFA model feature name, types of metabolic network information, metabolic condition information, MFA result information and MFA visualization information, a data type and a storing method.

The MFA object authoring tool includes: a means of inputting a new MFA object name, metabolic network information, metabolic condition information, MFA result information and MFA visualization information; and a means of changing the related existing MFA object name, metabolic network information, metabolic condition information, MFA result information and MFA visualization information.

The MFA object analysis browser includes: a means of parsing the DTD or schema file of XML generated by the MFA model feature authoring tool to obtain information about a data format and the MFA model feature; a means of parsing the XML file generated by the MFA object authoring tool to obtain information about the MFA object; a means of visualizing the obtained information in a text or graph form to output; and a means of performing MFA based on the obtained information and visualizing the MFA result in a text or graph form to output, or visualizing by combining the MFA result with the obtained information in a text or graph form to output.

In another aspect, the present invention provides a method for operating an MFA information system capable of generating, editing, storing and visualizing an MFA model feature and an MFA object and editing, storing and visualizing the result obtained by performing MFA based on the MFA object. The method comprises: (a) the first step of generating a new MFA model feature or generating a DTD or schema file of XML after collecting and editing the corresponding existing MFA model feature; (b) the second step of generating a new MFA object with reference to the generated DTD or schema file of XML or editing the corresponding existing MFA object to store the MFA object in an XML file; (c) the third step of reading the DTD or schema file of XML generated in the first step and the XML file stored in the second step to visualize the MFA object; and (d) the fourth step of carrying out MFA based on the MFA object visualized in the third step, editing, storing and visualizing the MFA result.

In the method for operating the MFA information system, the first step comprises (i) the first sub-step of defining a new MFA model feature name, types of metabolic network information, metabolic condition information, MFA result information and MFA visualization information, a data type and a storing method; and (ii) the second sub-step of collecting and editing related existing information to change an MFA model feature name, types of metabolic network information, metabolic condition information, MFA result information and MFA visualization information, a data type and a storing method.

The second step comprises (i) the first sub-step of inputting a new MFA object name, metabolic network information, metabolic condition information, MFA result information and MFA visualization information; and (ii) the second sub-step of changing the corresponding existing MFA model object name, metabolic network information, metabolic condition information, MFA result information and MFA visualization information.

The first and second steps comprise storing the result defined in the first sub-step and the result changed in the second sub-step in a DTD or schema file of XLM, respectively.

The third step comprises (i) the first sub-step of parsing the DTD or schema file of XML generated in the first step to obtain information about a data format and the MFA model feature; (ii) the second sub-step of parsing the XML file generated in the second step to obtain information about the MFA object; and (iii) the third sub-step of visualizing the information obtained in the first and second sub-steps in a text or graph form to output.

The fourth step comprises (i) the first sub-step of performing MFA based on the information obtained in the first and second sub-steps of the third step; and (ii) the second sub-step of visualizing only the result of the first sub-step in a text or graph form or visualizing by combining the result of the first sub-step with the existing information in a text or graph form to output.

Furthermore, the present invention provides an operating method of an MFA model feature authoring tool used in an MFA information system. The operating method comprises: the first step of generating the basic structure of a new DTD or schema for MFA or retrieving the existing DTD or schema; the second step of inputting a new MFA model feature into the DTD or schema for MFA, editing or deleting the MFA model feature; the third step of inputting, editing or deleting the attribute of each MFA model feature; the fourth step of determining whether said each feature and corresponding attribute need to be stored after they are inputted or edited; and the fifth step of storing said each feature and corresponding attribute in a DTD or schema file for MFA when it is determined that they need to be stored but returning to the second step when it is determined that they do not need to be stored.

In the above operating method, the second step comprises inputting, editing or deleting the MFA model feature by inputting or editing the feature name or feature data type, and the third step comprises inputting, editing or deleting the attribute by inputting or editing the attribute name and attribute type.

Moreover, the present invention also provides an operating method of an MFA object authoring tool used in an MFA information system. The operating method comprises: the first step of generating a new MFA object primitive, inputting the name and type of the MFA object primitive, and determining whether the inputted values need to be stored or not; the second step of returning to the first step when it is determined that the inputted values do not need to be stored but retrieving a DTD or schema for MFA, generated by an MFA model feature authoring tool, when it is determined that the inputted values need to be stored; the third step of selecting a feature to be stored among the retrieved DTD or schema and inputting the external appearance of the selected feature to be visualized; the fourth step of inputting an MFA object name and the attribute value of the MFA object according to definition by the DTD or schema for MFA; the fifth step of determining whether information about the inputted MFA object needs to be stored or not; and the sixth step of returning to the first step when it is determined that the information about the inputted MFA object does not need to be stored but storing the information in XML when it is determined that it needs to be stored.

Furthermore, the present invention provides an operating method of an MFA object analysis browser used in an MFA information system. The operating method comprises: the first step of inputting a DTD or schema (A) generated by an MFA model feature authoring tool and an XML file (B) generated by an MFA object authoring tool and performing file parsing; the second step of constructing information about the parsed MFA object in a text or graph form for an internal data structure and visualization and determining whether MFA needs to be performed or not; the third step of visualizing the MFA object information when it is determined that MFA does not need to be performed but carrying out MFA based on the information generated in the second step, inputting and visualizing MFA result information when it is determined that MFA needs to be performed; the fourth step of determining whether the information needs to be stored; and the fifth step of returning to the second step when it is determined that the information does not need to be stored but storing the information in the XML when it is determined that the information needs to be stored.

The present invention also provides a computer readable recording medium storing a program executing a method of operating an MFA information system. The program comprises the steps of: (a) defining a new MFA model feature name, types of metabolic network information, metabolic condition information, MFA result information and MFA visualization information, a data type and a storing method, collecting and editing related existing information to change an MFA model feature name, types of metabolic network information, metabolic condition information, MFA result information and MFA visualization information, a data type and a storing method, and storing the defined result and the changed result in a DTD or schema file of XML; (b) generating a new MFA object with reference to the DTD or schema file of XML generated in said step (a) or editing the existing MFA object, storing the MFA object in an XML file, inputting a new MFA object name, metabolic network information, metabolic condition information, MFA result information and MFA visualization information, and changing the existing MFA model object name, metabolic network information, metabolic condition information, MFA result information and MFA visualization information; (c) storing the inputted result and the changed result in said step (b) in the XML file; (d) parsing the generated DTD or schema file of XML to obtain information about a data format and an MFA model feature and parsing the XML file to obtain information about the MFA object; (e) visualizing the information obtained in said step (d) in text and graph (node and edge) forms to output; and (f) performing MFA based on the obtained information in said step (d) and visualizing the MFA result in a text or graph form or visualizing by combining the MFA result with the existing information in a text or graph form to output.

"MFA model feature" used in the present invention corresponds to a class for grouping or classifying elements for representing MFA. The MFA model feature is composed of metabolic network information, metabolic condition information, MFA result information and MFA visualization information. Detailed contents of the information are different depending on MFA features.

For example, the feature 'reaction' has metabolic network information such as 'name of reaction', 'reversibility of reaction', 'name of reactant', 'stoichiometry of reactant' and so on and metabolic condition information such as the influence according to an addition or removal of genes for representing a reaction constraint condition, a minimum or maximum range of a corresponding flux and flux measurement values and so on. Furthermore, there are MFA result information representing flux values and MFA results after MFA and metabolic flux visualization information representing position coordinates, shapes and colors of nodes and edges on a graph.

"MFA object" corresponds to data composed according to an MFA model feature and it is an example of the realized form of the MFA feature. For example, MFA objects for the MFA model feature 'reaction' include 'glycolysis', 'glyoxylate metabolism' and 'oxidative phosphorylation'.

Other aspects, features and advantages of the invention will be more fully apparent from the ensuing disclosure and appended claims.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE INVENTION AND PREFERRED EMBODIMENT THEREOF

Reference will now be made in detail to the preferred embodiments of the present invention, examples of which are illustrated in the accompanying drawings.

Figure 1:
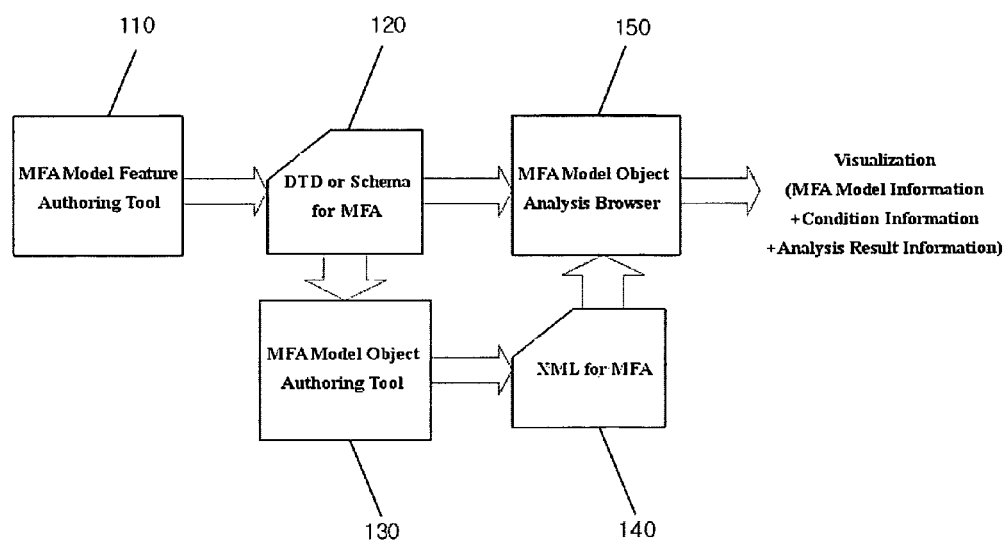
FIG. 1 illustrates the configuration of a system capable of generating, editing, storing and visualizing an MFA model feature and an MFA object using an XML and generating, editing, storing and visualizing the result obtained by performing MFA based on the object according to the present invention.

FIG. 1 illustrates the configuration of a system capable of generating, editing, storing and visualizing an MFA model feature and an MFA object using XML and generating, editing, storing and visualizing the MFA result obtained by performing MFA based on the object according to the present invention. The system includes an MFA model feature authoring tool 110 for generating, editing and storing a DTD or schema for MFA, a new DTD or schema file 120 for MFA, generated, edited and stored by the MFA model feature authoring tool 110, an MFA object authoring tool 130 for generating, editing and storing an MFA object in response to the DTD or schema for MFA, an XML file 140 generated, edited and stored by the MFA object authoring tool 130, and an MFA object analysis browser 150 for reading the DTD or schema file for MFA and the XML file, visualizing the MFA object, performing MFA and visualizing the MFA result.

The MFA model feature authoring tool 110 is a system module for authoring an MFA model feature. The MFA model feature authoring tool 110 generates a new MFA model feature or collects and edits the existing MFA model feature, and generates a DTD or schema file of the XML. The MFA model feature is generated by defining the name of the new MFA model feature and types of metabolic network information, metabolic condition information, MFA result information and MFA visualization information, a data type, and a storing method.

The edition of the MFA model feature is performed by changing the name of the existing MFA model feature and types of metabolic network information, metabolic condition information, MFA result information and MFA visualization information, a data type and a storing method.

The DTD or schema file 120 for MFA is a new file generated or a file edited and then stored by the MFA model feature authoring tool 110 and it has a structure capable of storing MFA model features.

The MFA object authoring tool 130 is a system module for authoring an MFA object. The MFA object authoring tool 130 generates a new MFA object in response to the DTD or schema for MFA or collects and edits the existing MFA objects and stores them in the XML.

The MFA object is generated by inputting the name of the MFA object, metabolic network information, metabolic condition information, MFA result information and MFA visualization information in response to DTD or schema for MFA. The edition of the MFA object is carried out by changing the name of the corresponding existing MFA object, metabolic network information, metabolic condition information, MFA result information and MFA visualization information. This function of authoring the MFA object is executed by generating, editing and storing an XML file.

The XML file 140 is a new file generated or a file edited and then stored by the MFA object authoring tool 130 and it stores MFA objects in a structure defined by the DTD or schema for MFA.

The MFA object analysis browser 150 is a system module which parses the DTD or schema file 120 for MFA and the XML file 140 to visualize the MFA object, performs MFA based on the visualized MFA object, and visualizes and stores the MFA result. The MFA object analysis browser 150 reads and parses the DTD or schema file 120 for MFA to obtain information about a data format and the MFA model feature, and then reads the XML file 140 to acquire information about the MFA object. The obtained information is visualized in text and graph (node and edge) forms and output. Furthermore, MFA is performed based on the information and the MFA result is visualized in a text or graph form and output. Otherwise, the MFA result is integrated with the MFA object information obtained by reading the XML file 140, visualized in a text or graph form, and output or stored.

Figure 2:
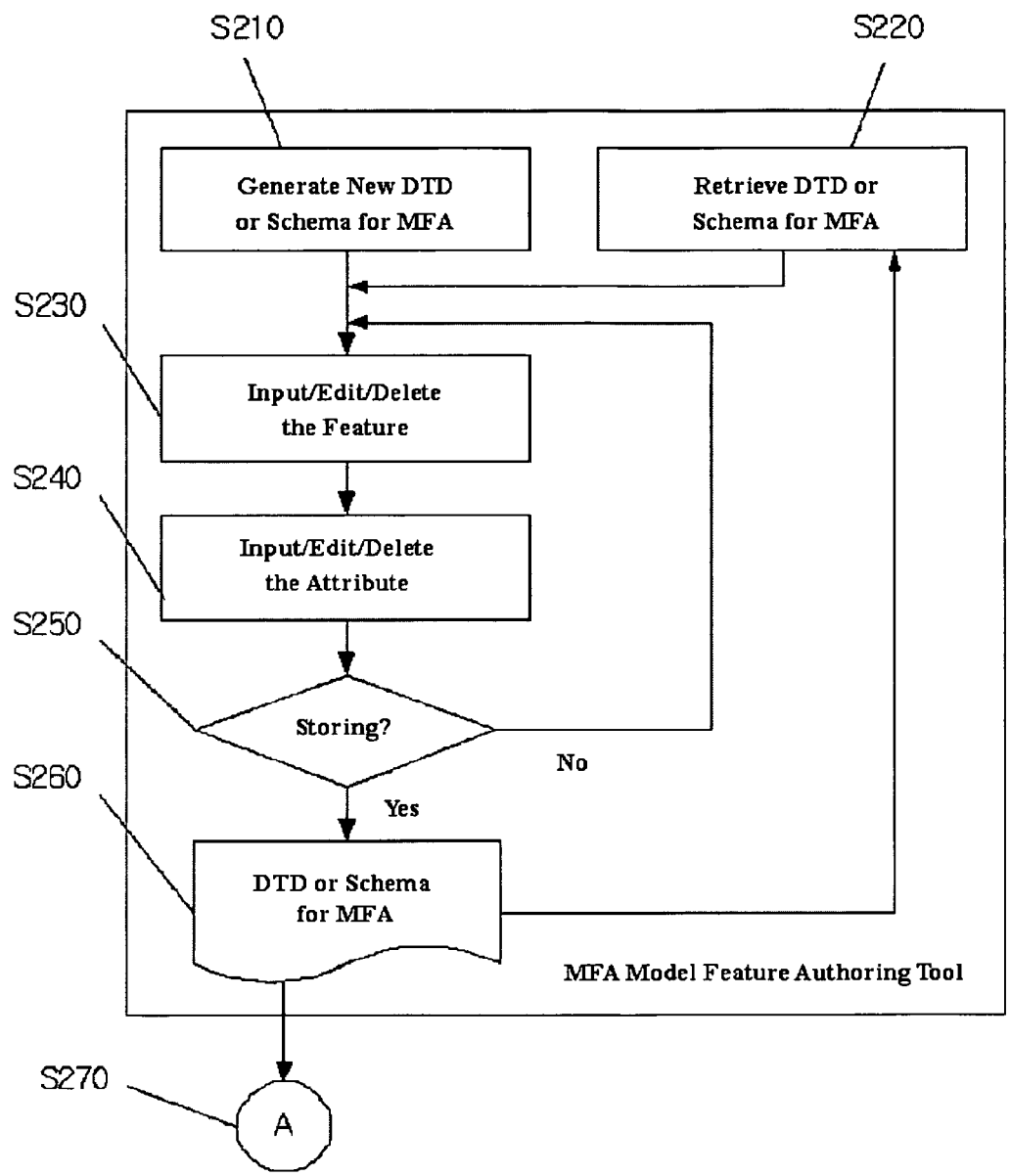
FIG. 2 is a flow chart showing an operation process of an MFA model feature authoring tool.

FIG. 2 is a flow chart showing an operation process of the MFA model feature authoring tool 110. Referring to FIG. 2, the basic structure of a new DTD or schema for MFA is generated in the step S210. Here, the generated DTD or schema for MFA has only a basic frame for storing an MFA model feature and does not include detailed information about the MFA model feature. The existing DTD or schema for MFA can be retrieved instead of generating a new DTD or schema for MFA.

Subsequently, a new MFA model feature is inputted to the generated DTD or schema for MFA, and edited or deleted in the step S230. An operation of inputting or editing the MFA model feature includes an operation of inputting or editing an MFA model feature name and a feature data type. The MFA model feature name can be composed of a discretionary character string. The feature data type is selected from MFA object primitives made for modeling an MFA object. Here, the MFA object primitives can be composed of combinations of primitive units.

Each MFA model feature can have one or multiple attributes. Thus, the attribute (or attributes) of each feature is inputted, edited or deleted in the step S240. In the operation of inputting and editing the attribute, the attribute name and attribute type are inputted or edited. When the corresponding feature and attribute are inputted or edited in the steps S230 and S240, it is determined whether the result needs to be stored or not in the step S250. When it is determined that the result needs to be stored, the result is stored in a DTD or schema file for MFA in the step S260. The stored DTD or schema for MFA is retrieved in the step S220 or used in the input A of the MFA object authoring tool or the MFA object analysis browser in the step S270. When it is determined that the result does not need to be stored in the step S250, the process returns to the step S230.

Figure 3:
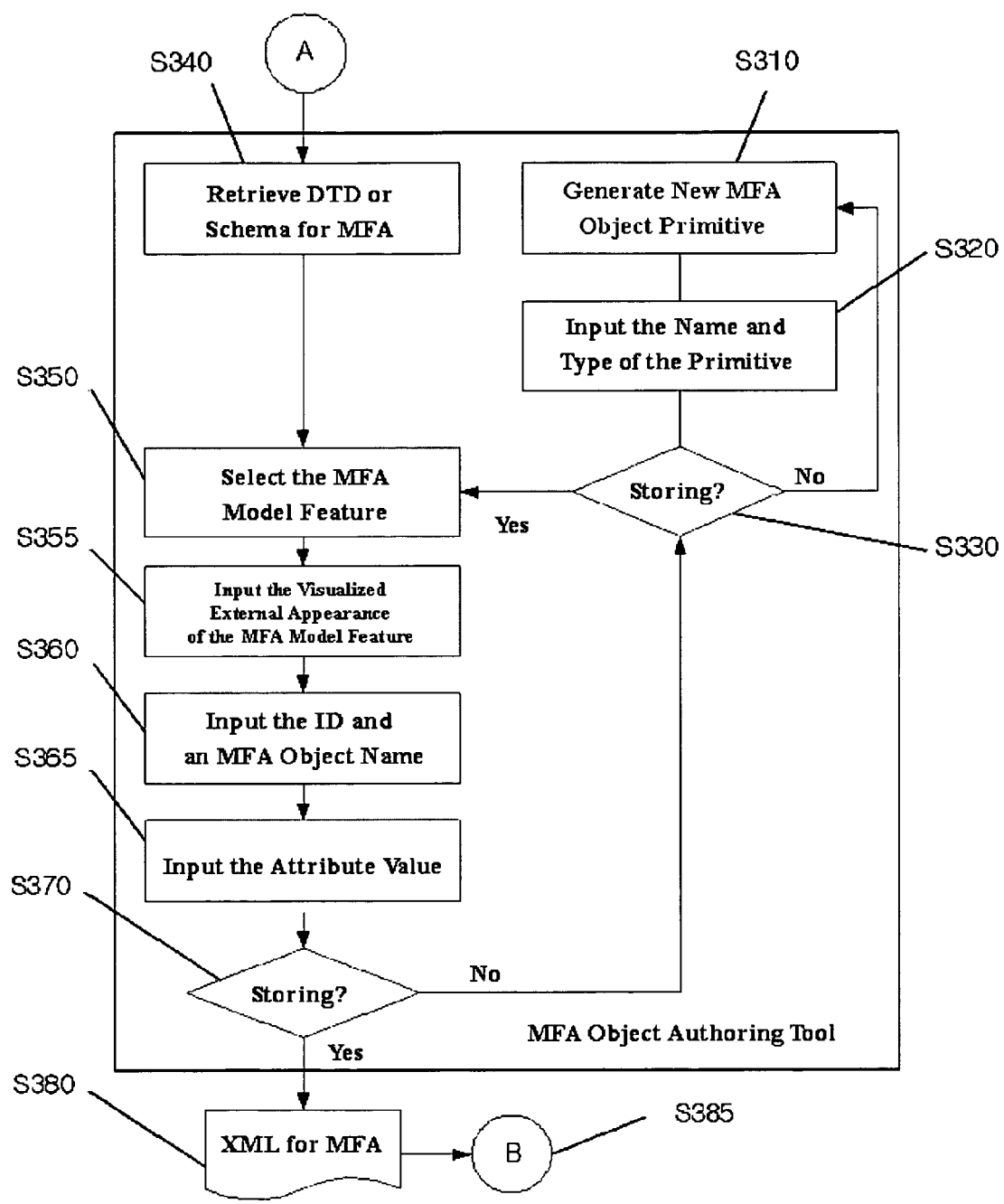
FIG. 3 is a flow chart showing an operation process of an MFA object authoring tool.

FIG. 3 is a flow chart showing an operating process of the MFA object authoring tool 130. Referring to FIG. 3, a new MFA object primitive is generated in the step S310, and than the name and type of the MFA object primitive are inputted in the step S320. In the step S330, it is determined whether the values inputted in the step S320 need to be stored or not. When it is determined that the values do not need to be stored in the step S330, the process returns to the step S310. When it is determined that the values need to be stored, the DTD or schema for MFA, generated in the MFA model feature authoring tool, is retrieved in the step S340, and then an MFA model feature to be stored is selected in the step S350. In the step S355, the external appearance of the selected feature to be visualized is determined. Specifically, the shape, color and transparency of the feature are inputted.

Subsequently, the ID and name of an MFA object are inputted in the step S360, and the attribute value of the MFA object is inputted according to definition by the DTD or schema for MFA in the step S365. Then, it is determined whether information about the inputted MFA object needs to be stored or not in the step S370. The process returns to the step S330 when it is determined that the information does not need to be stored but the information is stored in an XML form when it is determined that the information needs to be stored in the step S380.

Figure 4:
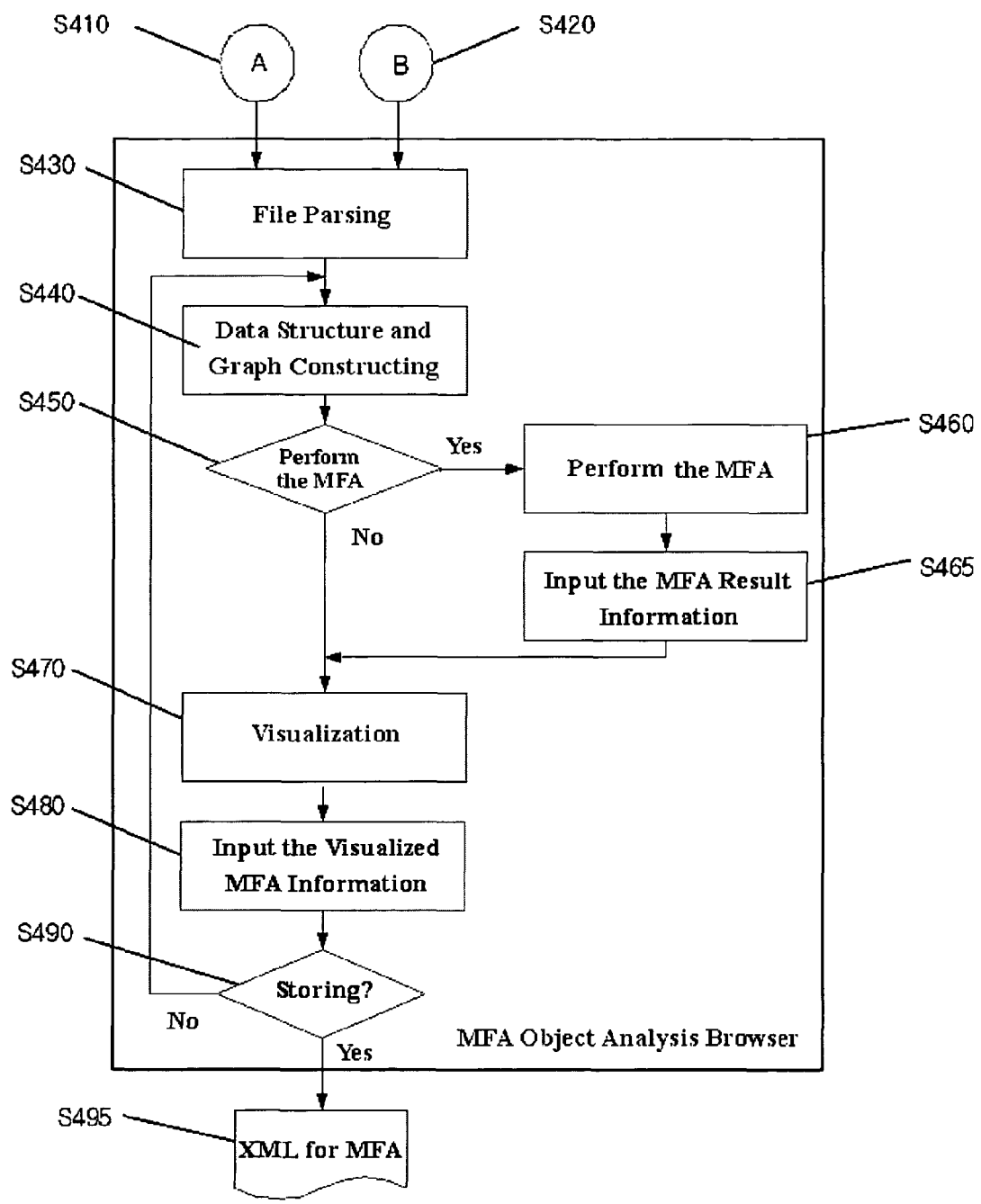
FIG. 4 is a flow chart showing an operation process of an MFA object analysis browser.

FIG. 4 is a flow chart showing an operation process of the MFA object analysis browser (150). Referring to FIG. 4, the DTD or schema (A) for MFA generated in the MFA model feature authoring tool and the XMA file (B) generated in the MFA object authoring tool are inputted in the steps S410 and S420, and file parsing is performed in the step S430.

Subsequently, information about the parsed MFA object is constructed in a graph form for an internal data structure and visualization in the step S440, and it is determined whether MFA is required or not in the step S450. When it is determined that MFA is not required, the information about the MFA object is visualized in the step S470. The information can be visualized even in a text form. In the step S460, MFA is performed based on the information generated in the step S440 when it is determined that MFA is needed. Then, MFA result information is inputted in the step S465 and visualized in the step S470.

Subsequently, MFA visualization information is inputted in the step S480, and it is determined whether the MFA visualization information needs to be stored or not in the step S490. The process returns to the step S440 when it is determined that the information does not need to be stored. When it is determined that the information needs to be stored, the information is stored in the XML in the step S495.

Figure 5:
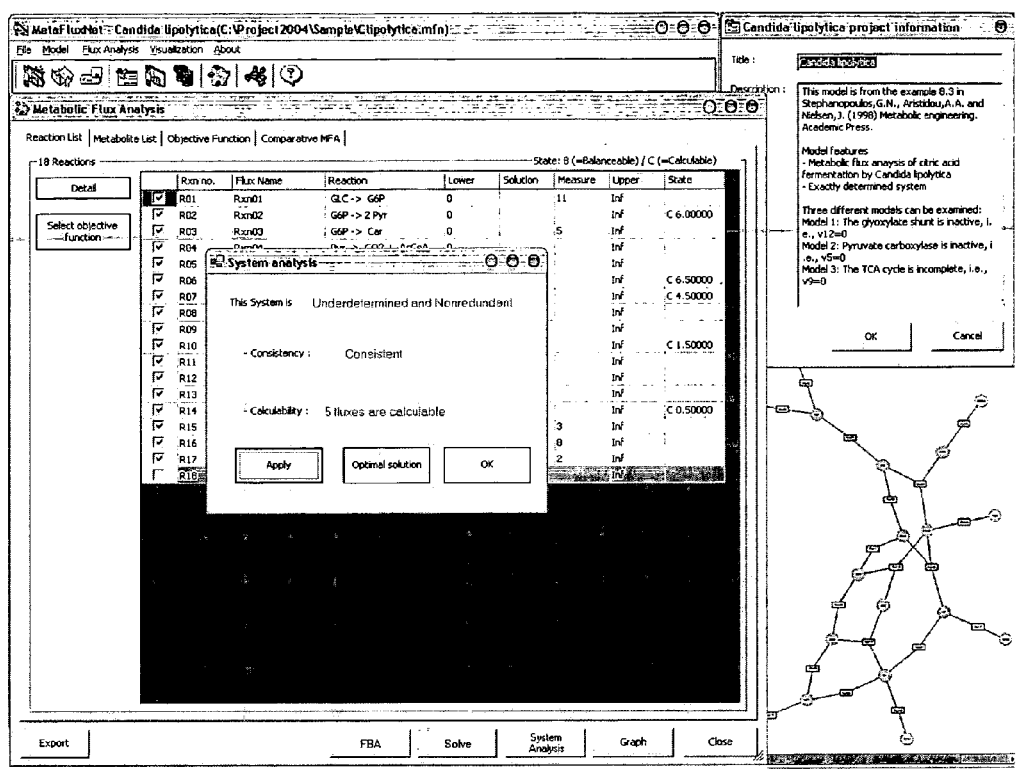
FIG. 5 shows a computer screen that can be seen while the MFA information system according to the present invention is operated.

FIG. 5 shows a computer screen that can be seen while the MFA information system according to the present invention is operated.

The above-described information system and the operating method thereof according to the present invention can be recorded on a computer readable recording medium and processed by a computer.

As described above, the present invention provides the MFA information system and method capable of generating, editing, storing and visualizing MFA model features and MFA objects using XML. Accordingly, the present invention can facilitate performing MFA by utilizing advantages of XML, such as transplantation, reusability, deciphering, scalability, flexibility and effective data exchange, and thus the present invention can be applied to strain improvement using metabolic engineering.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. An MFA (Metabolic Flux Analysis) information system comprising a computer operatively arranged with a computer readable medium storing a program executable by said computer for generating, editing, storing and visualizing an MFA model feature and an MFA object and editing, storing and visualizing the result obtained by performing MFA based on the MFA object, the system comprising:

an MFA model feature authoring tool for generating a DID (Document Type Definition) or schema file of XML (eXtensible Markup Language) from an MFA model feature, wherein the MFA model feature comprising metabolic network information, metabolic condition information, MFA result information and MFA visualization information is generated, collected and edited prior to generation of the DID or schema file of XML;

an MFA object authoring tool for generating a new MFA object with reference to the DID or schema file of XML generated by the MFA model feature authoring tool or storing an edited MFA object in the XML file after editing the existing MFA object; and an MFA object analysis browser for reading the DID or schema file of XML generated by the MFA model feature authoring tool and the XML file stored by the MFA object authoring tool to visualize the MFA object, carrying out MFA based on the MFA object to obtain an MFA result, and visualizing by integrating the MFA result with MFA object information; and wherein the MFA model feature authoring tool comprises:

a means of defining a new MFA model feature name, types of metabolic network information, metabolic condition information, MFA result information, MFA visualization information, a data type and a storing method to obtain a defined MFA result; and a means of changing the related existing MFA model feature name, types of metabolic network information, metabolic condition information, MFA result information, MFA visualization information, a data type and a storing method of the edited MFA model feature to obtain a changed MFA result.

2. The MEA information system according to claim 1, wherein the MEA object authoring tool comprises:

a means of inputting a new MEA object name, metabolic network information, metabolic condition information, MEA result information and MEA visualization information; and a means of changing the related existing MEA object name, metabolic network information, metabolic condition information, MEA result information and MEA visualization information.

3. The MEA information system according to claim 1, wherein the MEA object analysis browser comprises:

a means of parsing the DID or schema file of XML generated by the MEA model feature authoring tool to obtain information about a data format and the MEA model feature;

a means of parsing the XML file generated by the MEA object authoring tool to obtain information about the MEA object;

a means of visualizing the obtained information in a text or graph form to output; and a means of performing MEA based on the obtained information and visualizing the MEA result in a text or graph form, or visualizing by combining the MEA result with the obtained information in a text or graph form to output.

4. A method for operating an MFA (Metabolic Flux Analysis) information system capable of generating, editing, storing and visualizing an MFA model feature and an MFA object and editing, storing and visualizing the result obtained by performing MFA based on the MFA object, the method comprising the steps of:

(a) a first step of generating a DID (Document Type Definition) or schema file of XML (eXtensible Markup Language) from an existing MFA model feature, wherein the existing MFA model feature comprising metabolic network information, metabolic condition information, MFA result information and MFA visualization information is generated, collected and edited prior to generation of the DID or schema file of XML within an MFA model feature authoring tool;

(b) a second step of generating a new MFA object with reference to the generated DID or schema file of the XML and storing the MFA object in an XML file after editing an existing MFA object;

(c) a third step of reading the DID or schema file of the XML generated in the first step and the XML file stored in the second step to visualize the MFA object; and (d) a fourth step of carrying out MFA based on the MFA object visualized in the third step (c) to obtain an MFA result, editing, storing and visualizing the MFA result; and wherein the first step comprises:

(i) a first sub-step of defining a new MFA model feature name, types of metabolic network information, metabolic condition information, MFA result information, MFA visualization information, a data type and a storing method, to obtain a defined MFA result; and (ii) a second sub-step of collecting and editing related existing information to change an MFA model feature name, types of metabolic network information, metabolic condition information, MFA result information, MFA visualization information, a data type and a storing method of the edited MFA model feature, to obtain a changed MFA result.

5. The method according to claim 4, wherein the first step comprises storing the result defined in the first sub-step and the result changed in the second sub-step in a DID or schema file of XML.

6. The method according to claim 4, wherein the second step comprises:
   (i) a first sub-step of inputting a new MEA object name, metabolic network information, metabolic condition information, MEA result information and MEA visualization information; and
   (ii) a second sub-step of changing the corresponding existing MEA model object name, metabolic network information, metabolic condition information, MEA result information and MEA visualization information.

7. The method according to claim 6, wherein the second step comprises storing the result inputted in the first sub-step and the result changed in the second sub-step in an XLM file.

8. The method according to claim 4, wherein the third step comprises:
   (i) a first sub-step of parsing the DID or schema file of XML generated in the first step to obtain information about a data format and the MEA model feature;
   (ii) a second sub-step of parsing the XML file generated in the second step to obtain information about the MEA object; and
   (iii) a third sub-step of visualizing the information obtained in the first and second sub-steps in a text or graph form to output.

9. The method according to claim 8, wherein the fourth step comprises:
   (i) a first sub-step of performing MEA based on the information obtained in the first and second sub-steps of the third step; and
   (ii) a second sub-step of visualizing the result of the first sub-step in a text or graph form or visualizing by combining the result of the first sub-step with the existing information in a text or graph form to output.

10. A computer readable recording medium storing a program for executing a method of operating an MFA (Metabolic Flux Analysis) information system comprising:
   (a) defining a new MFA model feature name, types of metabolic network information, metabolic condition information, MFA result information, MFA visualization information, a data type and a storing method, to obtain a defined MFA result;
   (b) collecting and editing related existing information to change the MFA model feature name, types of metabolic network information, metabolic condition information, MFA result information, MFA visualization information, a data type and a storing method, to obtain a changed MFA result; and
   (c) storing the defined MFA result and the changed MFA result in a DID (Document Type Definition) or schema file of XML, wherein the DID or schema file of XML is generated from a generated MFA model feature comprising metabolic network information, metabolic condition information, MFA result information and MFA visualization information;
   (d) generating a new MFA object with reference to the generated DID or schema file of the XML generated in said step (c) and editing an existing MFA object, storing the MFA object in an XML file, inputting a new MFA object name, metabolic network information, metabolic condition information, MFA result information, MFA visualization information, and changing the existing MFA model object name, metabolic network information, metabolic condition information, MFA result information and MFA visualization information;
   (e) storing the data inputted and the data changed in said step (d) in the XML file;
   (f) parsing the generated DID or schema file of XML to obtain information about a data format and the MFA model feature and parsing the XML file to obtain information about the MFA object;
   (g) visualizing the information obtained in said step (I) in text and graph forms (node and edge) to output; and
   (h) performing MFA based on the information obtained in said step (I) to obtain an MFA result, and visualizing the MFA result in a text or graph form or visualizing by combining the MFA result with the existing information in a text or graph form to output.

* * * * *